(12) United States Patent
Khawaled et al.

(10) Patent No.: US 7,925,351 B2
(45) Date of Patent: Apr. 12, 2011

(54) GASTROINTESTINAL DEVICE FOR TREATING OBESITY AND DIABETES

(75) Inventors: Radwan Khawaled, Shafar-Am (IL); Jacob Benarie, Haifa (IL); Yossi Gross, Moshav Mazor (IL)

(73) Assignee: Betastim, Ltd., Caesarea (IL)

(*) Notice: Subject to any disclaimer, the term of this patent is extended or adjusted under 35 U.S.C. 154(b) by 479 days.

(21) Appl. No.: 12/138,874

(22) Filed: Jun. 13, 2008

(65) Prior Publication Data
US 2009/0030473 A1 Jan. 29, 2009

Related U.S. Application Data

(60) Provisional application No. 60/934,572, filed on Jun. 13, 2007.

(51) Int. Cl.
*A61N 1/00* (2006.01)
(52) U.S. Cl. ........................................................ 607/40
(58) Field of Classification Search ............... 607/40
See application file for complete search history.

(56) References Cited

U.S. PATENT DOCUMENTS

| | | | |
|---|---|---|---|
| 3,656,997 | A | 4/1972 | Cordes |
| 5,263,480 | A | 11/1993 | Wernicke et al. |
| 5,690,691 | A | 11/1997 | Chen et al. |
| 6,579,301 | B1 | 6/2003 | Bales et al. |
| 6,600,953 | B2 * | 7/2003 | Flesler et al. ............ 607/40 |
| 6,709,388 | B1 | 3/2004 | Mosse et al. |
| 6,776,999 | B1 | 8/2004 | Krumme |
| 2003/0055466 | A1 | 3/2003 | Ben-Haim et al. |
| 2003/0181958 | A1 | 9/2003 | Dobak, III |
| 2004/0176685 | A1 | 9/2004 | Takizawa et al. |
| 2005/0137633 | A1 | 6/2005 | Salo et al. |
| 2007/0078494 | A1 * | 4/2007 | Mintchev ............ 607/40 |

FOREIGN PATENT DOCUMENTS

| | | |
|---|---|---|
| WO | WO 97/26042 | 7/1997 |
| WO | WO 97/31679 | 9/1997 |
| WO | WO 01/91854 A1 | 12/2001 |
| WO | WO 2005/007232 | 1/2005 |
| WO | WO 2006/064503 A2 | 6/2006 |

OTHER PUBLICATIONS

Supplementary European Search Report dated Sep. 11, 2009, which issued during the prosecution of Applicants' European Patent Application No. EP 06 76 6139.
An Office Action dated Aug. 19, 2009, which issued during the prosecution of Applicants' U.S. Appl. No. 11/279,355.
An Office Action dated Aug. 19, 2009, which issued during the prosecution of Applicants' U.S. Appl. No. 11/965,997.
PCT International Preliminary Report on Patentability for PCT International Application No. PCT/IL2006/000819 issued Mar. 31, 2009.
Amaris et al., "Micropressor controlled movement of solid colonic content using sequential neural electrical stimulation," Gut 2002; 50; 475-479.
Park et al., "New Method of Moving Control for Wireless Endoscopic Capsule Using Electrical Stimuli," IEICE Trans. Fundamentals, vol. E88-A, No. 6 Jun. 2005; 1476-1480.

* cited by examiner

*Primary Examiner* — George Manuel
(74) *Attorney, Agent, or Firm* — RatnerPrestia (57) ABSTRACT

Apparatus is provided, including an ingestible capsule, one or more electrodes coupled to the capsule, and a control unit configured to maintain the capsule in a vicinity of a designated site of a subject by driving at least a subset of the electrodes to apply a current that induces reverse intestinal peristalsis in the subject. Other embodiments are also described.

82 Claims, 5 Drawing Sheets

GASTROINTESTINAL DEVICE FOR TREATING OBESITY AND DIABETES

CROSS-REFERENCES TO RELATED APPLICATIONS

This application claims priority from U.S. Provisional Patent Application 60/934,572 to Khawaled et al., entitled, "Gastrointestinal device for treating obesity and diabetes," filed on Jun. 13, 2007, which is incorporated herein by reference.

FIELD OF THE INVENTION

The present invention generally relates to ingestible apparatus. Specifically, the present invention relates to methods and apparatus that treat obesity and diabetes from within the gastrointestinal tract.

BACKGROUND OF THE INVENTION

The pathogenesis of obesity and diabetes in humans is attributed at least in part to alteration of regulation and homeostasis of glucose, fat, and protein metabolism, due to increased absorption by the gastrointestinal tract. The effects of dietary glucose, fat, and protein on the production, secretion, and action of hormones (including insulin) and cytokines (including leptin) mediating energy and glucose homeostasis in diabetes and obesity, may be mitigated by slowing digestive processes leading to their absorption and eventual metabolism.

PCT Publication WO 97/26042 to Terekhin et al., which is incorporated herein by reference, describes medical equipment that can be used, for example, in post-surgical therapy in outpatient clinics and in hospitals, as well as a prophylactic measure for treating alimentary tract diseases. The equipment is described as an electrical stimulant containing a capsule, in which are located consecutively-connected units for testing parameters of an external medium and a pulse driver, connected to a power supply. Electrodes are provided on the external surface of the capsule, and total in number (2+n), where n=0, 1, 2, etc.

PCT Publication WO 06/064503 to Belsky et al., which is incorporated herein by reference, describes apparatus for drug administration. The apparatus includes an ingestible capsule, which includes a drug, stored by the capsule. The apparatus is described as including an environmentally-sensitive mechanism, adapted to change a state thereof responsively to a disposition of the capsule within a gastrointestinal tract of a subject; one or more drug-passage facilitation electrodes; and a control component, adapted to facilitate passage of the drug, in response to a change of state of the environmentally-sensitive mechanism, by driving the drug-passage facilitation electrodes to apply an electrical current. The apparatus is described as further including a velocity-reduction element adapted to reduce a velocity of the capsule through the GI tract for at least a portion of the time that the control component is facilitating the passage of the drug.

PCT Publication WO 97/31679 to Dirin et al., which is incorporated herein by reference, describes electrostimulation of the gastrointestinal tract. Apparatus described comprises an olive-like or ovate-cylindrical body member in which at least a part of opposed hemispheres is made conducting and forms a pair of electrodes, as well as a pulse generator and an electric power supply source disposed inside the body member. The apparatus is described as comprising an electrode and means for cyclically reversing the polarity of pulses on the electrodes. Electrostimulation efficiency of the device is described as being independent of opposite preferential orientations of its body member within a given visceral organ of a human being or animal.

U.S. Pat. No. 6,709,388 to Mosse et al., which is incorporated herein by reference, describes a self-propelling device adapted to travel through a passage having walls containing contractile tissue, the device comprising a body and at least one contractile tissue-stimulating means for stimulating the walls to urge the device selectively. The stimulating means may be electrodes, and the passage can be the gut of an animal or human. The device is described as being particularly useful as an enteroscope.

The following patents and patent applications, which are incorporated herein by reference, may be of interest:

US Patent Application Publication 2003/0055466 to Ben-Haim et al.

U.S. Pat. No. 3,656,997 to Cordes et al.

U.S. Pat. No. 6,776,999 to Krumme et al.

PCT Patent Publication WO 01/91854 to Harel et al.

The following articles, which are incorporated herein by reference, may be of interest:

Amaris M et al., "Microprocessor controlled movement of solid colonic content using sequential neural electrical stimulation," Gut 50:475-479 (2002)

Park H et Al., "New methods of moving control for wireless endoscopic capsule using electrical stimulus," The 2004 International Technical Conference on Circuits/Systems, Computers and Communications, Hotel Taikanso, Sendai/Matsushima, Miyagi-ref., Japan, Jul. 6-8, (2004)

SUMMARY OF THE INVENTION

In some embodiments of the present invention, an ingestible capsule coupled to one or more electrodes is configured to remain in a designated region of the duodenum of a subject. Typically, at least one of the one or more electrodes comprises a sensor. In response to a sensing signal generated by the sensor, a control unit actuates a pulse generator which drives the electrodes to apply a current to intestinal muscle. Consequently, stimulation of reverse intestinal peristalsis and slowing of digestive processes of the subject are achieved. The control unit maintains the capsule in the region by driving the electrodes to induce repeated proximal motions of the capsule within the duodenum following respective distal motions of the capsule that are due to natural peristalsis.

For some applications, the one or more electrodes comprise one or more subsets of electrodes. The control unit drives a first subset of electrodes to induce reverse intestinal peristalsis, and drives a second set of electrodes to stimulate duodenal tissue in the designated region for reasons other than inducing peristalsis. Some suitable tissues are described hereinbelow.

In some embodiments, the control unit drives the same subset of electrodes to both induce reverse intestinal peristalsis as well as stimulate the tissue in the designated region.

For some applications, the capsule is configured to maintain itself in a vicinity of a pyloric sphincter of the subject for a predetermined duration of time by electrostimulating intestinal muscle to induce reverse intestinal peristalsis. In an embodiment, maintaining the capsule in the designated vicinity of the pyloric sphincter is achieved by stimulating intestinal muscle to induce reverse peristalsis until electromyography (EMG) sensing by the capsule indicates contractions of the pyloric sphincter. The induced reverse peristalsis is terminated until EMG sensing no longer indicates pyloric sphincter contractions, at which point (or after a delay) the inducing of reverse peristalsis is reinitiated. Alternatively or additionally, the application of current to induce reverse peristalsis is applied generally continuously for a designated period, or intermittently (e.g., according to a fixed schedule, or based on a sensed parameter of the gastrointestinal tract).

In an embodiment, the control unit is configured to drive a subset of electrodes to apply a stimulating current that induces contraction of the pyloric sphincter. Consequently, a rate of gastric emptying is reduced, thereby effectively reducing a rate of subsequent metabolism within intestine of the subject. Additionally, a feeling of satiety is induced within the subject because the volume of stomach contents remains high for a prolonged period.

In some embodiments, the capsule is configured to drive a current through a vagus nerve of the subject to induce contraction of the pyloric sphincter while the capsule is not adjacent thereto.

In some embodiments of the present invention, the ingestible capsule is configured to maintain itself in a segment of the duodenum in a vicinity of a sphincter of Oddi of the subject. Typically, maintaining the capsule in the designated vicinity is achieved in response to electromyography sensing of contractions of the sphincter of Oddi, e.g., detecting slow waves or spikes indicative of electrical activity of the sphincter. Alternatively or additionally, maintaining the capsule in the designated vicinity is achieved in response to pH sensing, wherein the capsule is configured to sense a pH indicative of digestive liquid from the pancreas and liver by way of the sphincter of Oddi. Upon identifying proximity of the capsule to the sphincter of Oddi, the control unit maintains the capsule in the vicinity by driving a first subset of electrodes to induce reverse intestinal peristalsis. The first subset of electrodes or a second subset of electrodes drives a current to stimulate the sphincter of Oddi, thereby inducing its contraction.

In some embodiments of the present invention, contraction of the sphincter of Oddi is stimulated by a current from one or more implantable electrodes configured to be implanted in the vicinity of the sphincter of Oddi.

Typically, contraction of the sphincter of Oddi is maintained for a predetermined amount of time such that it slows a release of digestive liquid designated for digesting food passing through the duodenum, effectively minimizing absorption of fats and carbohydrates by the small intestine of the subject.

In some embodiments of the present invention, the capsule is configured to stimulate a pancreas of the subject while maintaining itself in a segment of the duodenum which surrounds the pancreas of the subject. Typically, a first subset of electrodes is configured to induce reverse intestinal peristalsis subsequent to distal motions of the capsule that are due to natural peristalsis. In this manner, the capsule typically travels a plurality of times through the duodenum, cycling between distal and proximal motion, so as to increase the time that it is stimulating the pancreas. For some applications, a detecting sensor coupled to the capsule is configured to (a) detect blood glucose level, e.g., by detecting a state of the pancreas, or (b) to receive a transmitted signal indicative of blood glucose level of the subject. In response to the detecting or receiving, the control unit drives a second subset of electrodes to concomitantly stimulate the pancreas from the duodenum, and thereby modulate insulin production.

There is therefore provided, in accordance with an embodiment of the present invention, apparatus, including:
an ingestible capsule;
one or more electrodes coupled to the capsule; and
a control unit configured to maintain the capsule in a vicinity of a designated site of a subject by driving at least a subset of the electrodes to apply a current that induces reverse intestinal peristalsis in the subject.

In an embodiment, the one or more electrodes are configured to stimulate reverse peristalsis of intestine of the subject.

In an embodiment, the one or more electrodes include a plurality of electrodes.

In an embodiment, the control unit is configured to maintain the capsule in a vicinity of a sphincter of Oddi.

In an embodiment, the control unit is configured to maintain the capsule in a vicinity of the sphincter of Oddi of the subject for a period having a duration between 1 min and 30 min.

In an embodiment, the control unit is configured to maintain the capsule in a vicinity of the sphincter of Oddi of the subject for a period having a duration between 30 min and 180 min.

In an embodiment, the control unit is configured to maintain the capsule in the vicinity of the sphincter of Oddi by inducing repeated proximal motions of the capsule within a duodenum of the subject following respective distal motions of the capsule that are due to natural peristalsis.

In an embodiment, the control unit is configured to drive at least one of the one or more electrodes to apply a current that induces contraction of the sphincter of Oddi.

In an embodiment, the control unit is configured to maintain the capsule in a vicinity of a pyloric sphincter of the subject.

In an embodiment, the control unit is configured to maintain the capsule in a vicinity of the pyloric sphincter of the subject for a period having a duration between 1 min and 30 min.

In an embodiment, the control unit is configured to maintain the capsule in a vicinity of the pyloric sphincter of the subject for a period having a duration between 30 min and 180 min.

In an embodiment, the control unit is configured to induce a feeling of satiety of the subject by driving at least one of the one or more electrodes to apply a stimulating current that induces contraction of the pyloric sphincter.

In an embodiment, the control unit is configured to reduce a rate of gastric emptying of the subject by applying the stimulating current to the pyloric sphincter.

In an embodiment, the control unit is configured to maintain the capsule in a segment of the intestine that surrounds a pancreas of the subject, and the control unit is configured to stimulate the pancreas of the subject by driving at least one of the one or more electrodes to apply a stimulating current to the pancreas.

In an embodiment, the control unit is configured to maintain the capsule in the segment for a period having a duration between 1 min and 30 min.

In an embodiment, the control unit is configured to maintain the capsule in the segment for a period having a duration between 30 min and 180 min.

In an embodiment, the control unit is configured to maintain the capsule within the segment of the intestine by inducing repeated proximal motions of the capsule within a duodenum of the subject following respective distal motions of the capsule that are due to natural peristalsis.

In an embodiment, the apparatus includes a sensor configured to sense a location of the capsule and generate a signal in response thereto.

In an embodiment, the sensor is configured to detect electrical activity of a duodenum of the subject.

In an embodiment, the sensor is configured to detect slow waves indicative of the electrical activity.

In an embodiment, the sensor is configured to detect spikes indicative of the electrical activity.

In an embodiment, the capsule includes a pulse generator, and the pulse generator is configured to be activated in response to the signal.

In an embodiment, the pulse generator is configured to cyclically reverse polarity of a plurality of pulses driven through the one or more electrodes.

In an embodiment, the pulse generator is configured to generate a waveform having an amplitude of between 1 mA and 20 mA.

In an embodiment, the pulse generator is configured to generate a waveform having a pulse duration of between 100 us and 1000 us.

In an embodiment, the pulse generator is configured to generate a waveform having a pulse duration of between 1 ms and 10 ms.

In an embodiment, the pulse generator is configured to generate a waveform having a pulse frequency of between 1 Hz and 10 Hz.

In an embodiment, the pulse generator is configured to generate a waveform having a pulse frequency of between 10 Hz and 100 Hz.

In an embodiment, the pulse generator is configured to generate a waveform having a burst length of between 100 ms and 1 s.

In an embodiment, the pulse generator is configured to generate a waveform having a duration between bursts thereof of between 1 s and 10 s.

In an embodiment, the pulse generator is configured to be activated for a stimulation duration of between 1 min and 30 min.

In an embodiment, the pulse generator is configured to be activated for a stimulation duration of between 30 min and 180 min.

In an embodiment, the sensor includes at least one element selected from the group consisting of: a pH sensor, an electromyography sensor, and an accelerometer.

In an embodiment, the sensor includes the pH sensor, and the pH sensor includes at least one of the one or more electrodes.

In an embodiment, the sensor includes the electromyography sensor, and the electromyography sensor is configured to detect sphincter contraction.

In an embodiment, the sensor is configured to detect slow waves indicative of electrical activity of the sphincter.

In an embodiment, the sensor is configured to detect spikes indicative of electrical activity of the sphincter.

In an embodiment, the electromyography sensor is configured to detect a contraction of a sphincter of Oddi.

In an embodiment, the electromyography sensor is configured to detect contraction of a pyloric sphincter of the subject.

There is further provided, in accordance with an embodiment of the present invention, apparatus, including:

one or more implantable electrodes configured to be implanted at a sphincter of Oddi of a subject; and a control unit, configured to drive the electrodes to apply a current that induces contraction of the sphincter of Oddi.

In an embodiment, the control unit is configured to drive the one or more electrodes to apply the current to the sphincter of Oddi for a period having a duration between 1 min and 30 min.

In an embodiment, the control unit is configured to drive the one or more electrodes to apply the current to the sphincter of Oddi for a period having a duration between 30 min and 180 min.

There is yet further provided, in accordance with an embodiment of the present invention, a method, including:

inducing reverse intestinal peristalsis in a subject by electrical stimulation; and configuring the stimulation to maintain an ingestible capsule in a vicinity of a pyloric sphincter of the subject.

In an embodiment, the method includes ingesting the capsule prior to eating by the subject.

In an embodiment, the method includes ingesting the capsule prior to sleeping by the subject.

In an embodiment, configuring the stimulation to maintain the capsule in the vicinity of the pyloric sphincter includes identifying proximity of the capsule to the pyloric sphincter by sensing a contraction of the pyloric sphincter.

In an embodiment, the method includes driving a current into the pyloric sphincter configured to reduce a rate of gastric emptying of the subject.

In an embodiment, driving the current includes stimulating a vagus nerve of the subject.

In an embodiment, driving the current includes generating a waveform having a burst length of between 100 ms and 1000 ms.

In an embodiment, driving the current includes generating a waveform having a duration between bursts thereof of between 1 s and 10 s.

There is still further provided, in accordance with an embodiment of the present invention, a method, including:

inducing reverse intestinal peristalsis in a subject by electrical stimulation; and configuring the stimulation to maintain an ingestible capsule in a vicinity of a sphincter of Oddi of the subject.

In an embodiment, configuring the stimulation to maintain the capsule in the vicinity of the sphincter of Oddi includes identifying proximity of the capsule to the sphincter of Oddi by sensing a contraction of the sphincter of Oddi.

In an embodiment, sensing the contraction of the sphincter of Oddi includes electromyographically sensing.

In an embodiment, the method includes driving a current into the sphincter of Oddi configured to reduce emptying of a digestive liquid into a duodenum of the subject.

In an embodiment, maintaining the capsule includes sensing a parameter of external surroundings of the capsule, and generating a signal in response thereto.

In an embodiment, sensing the parameter of the external surroundings includes pH sensing.

In an embodiment, pH sensing includes:

detecting a pH of between 4.0 and 7.0 distal to the capsule; and identifying that the capsule is at a location within a duodenum of the subject distal to the sphincter of Oddi in response to the detecting.

In an embodiment, the method includes inducing a reverse peristaltic wave by stimulating muscle of the intestine in response to the identifying.

There is additionally provided, in accordance with an embodiment of the present invention, a method, including:

inducing reverse intestinal peristalsis in a subject by electrical stimulation; and configuring the stimulation to maintain an ingestible capsule in a segment of the small intestine surrounding a pancreas of the subject.

In an embodiment, maintaining the capsule in the segment includes inducing repeated proximal motions of the capsule within a duodenum of the subject following respective distal motions of the capsule.

In an embodiment, maintaining the capsule in the segment includes maintaining the capsule in the segment for a period having a duration between 1 min and 180 min.

In an embodiment, the method includes stimulating the pancreas by the capsule, when the capsule is in the segment.

In an embodiment, stimulating the pancreas includes modulating insulin production of the pancreas.

In an embodiment, the method includes detecting a state of the pancreas, and stimulating the pancreas includes stimulating the pancreas in response to the detecting.

The present invention will be more fully understood from the following detailed description of embodiments thereof, taken together with the drawings, in which:

DETAILED DESCRIPTION OF EMBODIMENTS

Figure 1A:
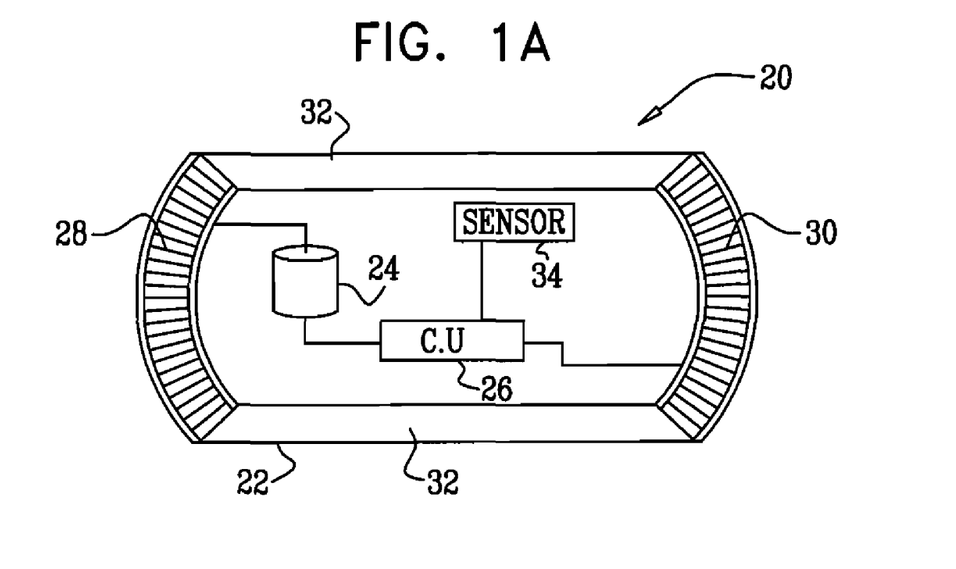
FIG. 1A is a schematic illustration of a lengthwise cross-section of an ingestible capsule comprising electrodes, in accordance with an embodiment of the present invention.

Reference is made to FIG. 1A, which is a schematic illustration of a lengthwise cross-section of apparatus 20 comprising an ingestible capsule 22 that comprises an electrode 28 and an electrode 30, in accordance with an embodiment of the present invention. Capsule 22 is configured to be ingested by a subject prior to, during, or following eating, or prior to sleeping. Once capsule 22 approaches a target vicinity within the gastrointestinal tract of the subject (e.g., a pyloric sphincter 52, a sphincter of Oddi 60, a duodenum 54, or a segment 70 of duodenum 54 surrounding a pancreas 56, as described hereinbelow), a sensor 34 detects proximity of capsule 22 to the desired vicinity and conveys a signal to a control unit 26 coupled to capsule 22. Sensor 34 comprises an electromyography sensor. Alternatively or additionally, sensor 34 comprises a pH sensor. Further alternatively or additionally, sensor 34 comprises an accelerometer configured for remote sensing indicative of the location of capsule 22 within intestine of the subject. Still further alternatively or additionally, sensor 34 senses a transmitted signal, indicating the location of capsule 22.

Control unit 26 is configured to maintain capsule 22 within the target vicinity of the gastrointestinal tract by driving a current between electrode 28 and electrode 30 to induce reverse intestinal peristalsis. Alternatively, the current is driven between electrode 28 or electrode 30 and another electrode (not shown) on the capsule. Electrode 28 and electrode 30 are located on the proximal and distal ends, respectively, of capsule 22. For some applications, control unit 26 determines the orientation of capsule 22 within the gastrointestinal tract by sensing electrical activity of the gastrointestinal tract at a plurality of sites on the capsule, or by sensing the direction of a peristaltic wave moving distally in the gastrointestinal tract, around the capsule. After determining the orientation of capsule 22 within the gastrointestinal tract, control unit 26 designates the electrode at the proximal end with respect to the gastrointestinal tract to be electrode 28, and the electrode on the distal end of capsule 22 to be electrode 30.

In an embodiment, the signal generated by sensor 34 actuates a pulse generator within control unit 26 which cyclically reverses polarity of a plurality of pulses driven through or between electrode 28 and electrode 30.

Typically, suitable electrical stimulation parameters are pre-programmed, or determined for a given subject. For example, ranges of parameters of a bipolar electrical stimulation may include some or all of the following:

Amplitude: 1-5 mA or 5-20 mA;
Pulse duration: 100-1000 us or 1-10 ms;
Pulse frequency: 1-10 Hz or 10-100 Hz;
Burst length: 100-300 ms or 300-1000 ms;
Time between bursts: 1-3 sec or 3-10 sec; and
Total stimulation duration: 1 min to 180 min.

Accordingly, proximal motion of capsule 22 within intestine of the subject is achieved, followed, upon termination of the signal, by distal motion of capsule 22 due to natural peristalsis (optionally supplemented by electrically-induced peristalsis). Repetitions of this procedure produce cycles of proximal and distal motion. Typically, control unit 26 drives a current between electrode 28 and electrode 30 that induces stimulation of a designated area within or outside of intestine of the subject, once capsule 22 has placed itself in the designated area.

Capsule 22 comprises a power source 24 which enables current to be driven between electrode 28 and electrode 30 and/or other electrodes of capsule 22. Additionally, capsule 22 typically comprises an insulator 32 configured for isolating electrode 28 and electrode 30.

Figure 1B:
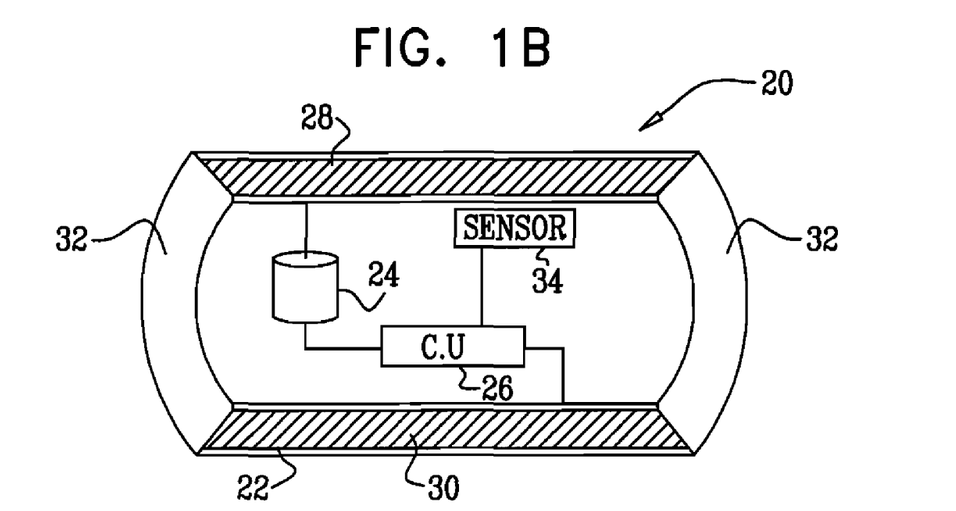
FIG. 1B is a schematic illustration of a lengthwise cross-section of the capsule, in accordance with another embodiment of the present invention.

Reference is now made to FIG. 1B, which is a schematic illustration of a lengthwise cross-section of capsule 22, as described hereinabove with reference to FIG. 1A, with the exception that electrode 28 and electrode 30 are disposed on a lengthwise surface of capsule 22, in accordance with an embodiment of the present invention.

Figure 1C:
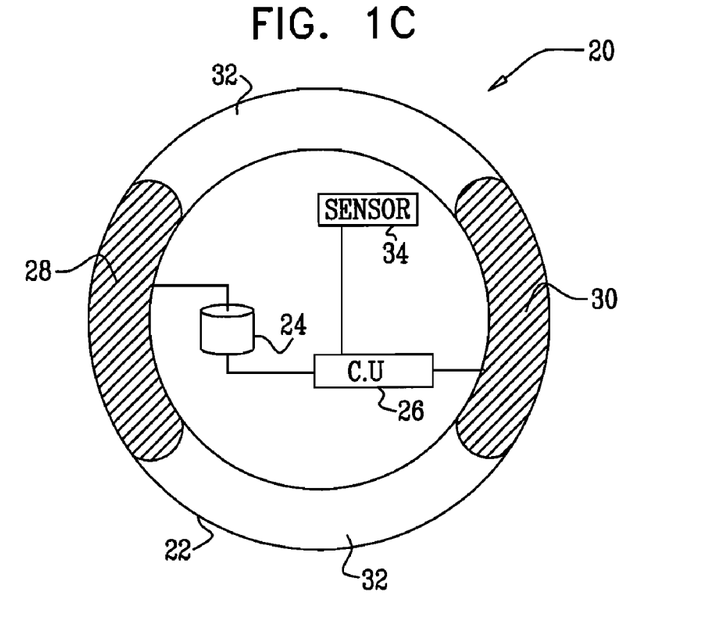
FIG. 1C is a schematic illustration of an axial cross-section of the capsule of FIG. 1B, in accordance with an embodiment of the present invention.

Reference is now made to FIG. 1C, which is a schematic illustration of an axial cross-section of capsule 22 as described hereinabove with reference to FIG. 1B, in accordance with an embodiment of the present invention.

Figure 1D:
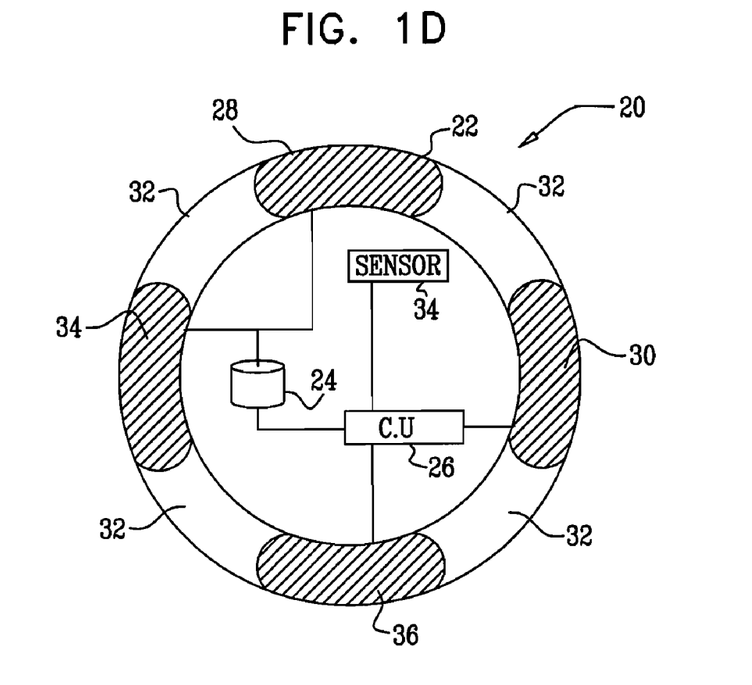
FIG. 1D is a schematic illustration of an axial cross-section of the capsule, in accordance with another embodiment of the present invention.

Reference is now made to FIG. 1D, which is a schematic illustration of capsule 22 as described hereinabove with reference to FIG. 1B, with the exception that an additional electrode 34 and a second additional electrode 36 are coupled to capsule 22, in accordance with an embodiment of the present invention. Control unit 26 is configured to drive a current between electrode 28 and electrode 30 (or between other electrodes) to induce reverse intestinal peristalsis by stimulating intestinal muscle. Once capsule 22 is disposed in the designated vicinity within the small intestine of the subject, control unit 26 drives a current between electrode 34 and electrode 36 that induces stimulation of a designated tissue within intestine of the subject or in a vicinity thereof. As appropriate, dedicated electrodes may be used for generating peristalsis, and other dedicated electrodes may be used for therapeutic tissue stimulation. Alternatively, there is at least some overlap between the two sets of electrodes.

Figure 2:
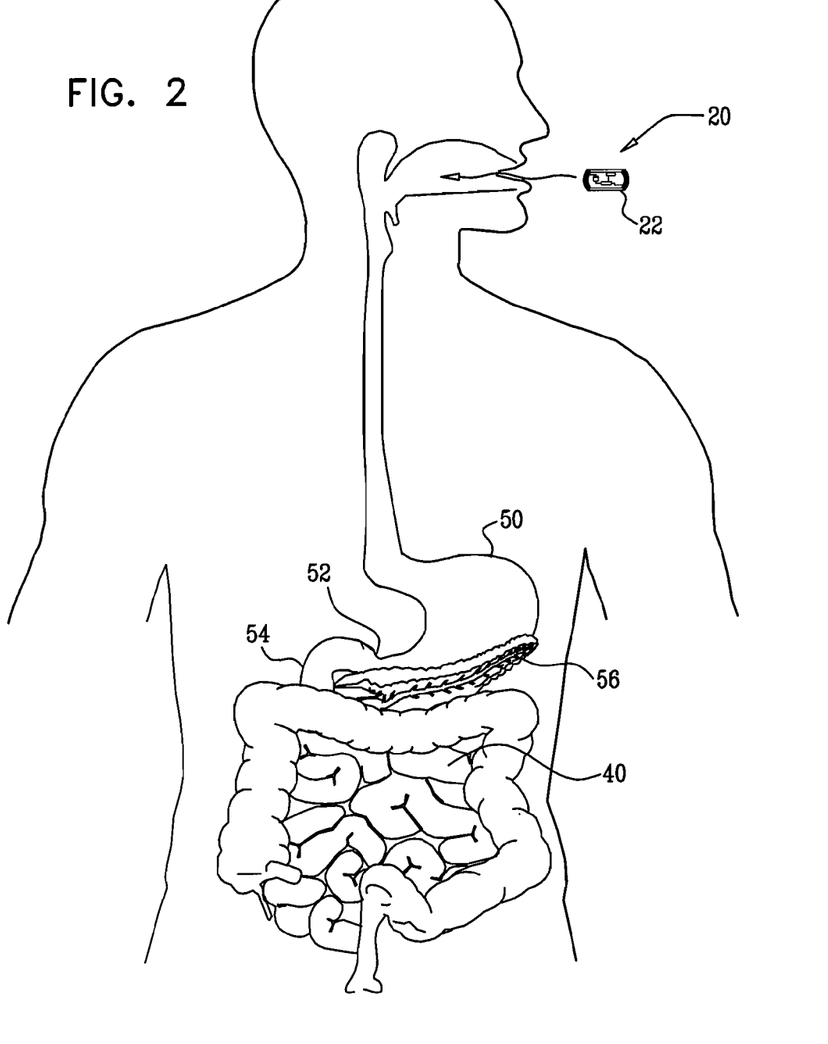
FIG. 2 is a schematic illustration of the capsule prior to ingestion, in accordance with an embodiment of the present invention.

Reference is now made to FIG. 2, which is a schematic illustration of apparatus 20 comprising capsule 22 being ingested by the subject, in accordance with an embodiment of the present invention. Capsule 22 is typically configured to extend its time of residence in a duodenum 54 of the small intestine 40 by driving current into the duodenum, as described hereinabove. In some embodiments of the present invention, described hereinbelow with reference to FIG. 4, capsule 22 is configured to stimulate a contraction of a pyloric sphincter 52 to slow gastric emptying of stomach 50 of the subject. In some embodiments of the present invention, described hereinbelow with reference to FIG. 6, capsule 22 is configured to stimulate the pancreas 56 of the subject.

Figure 3:
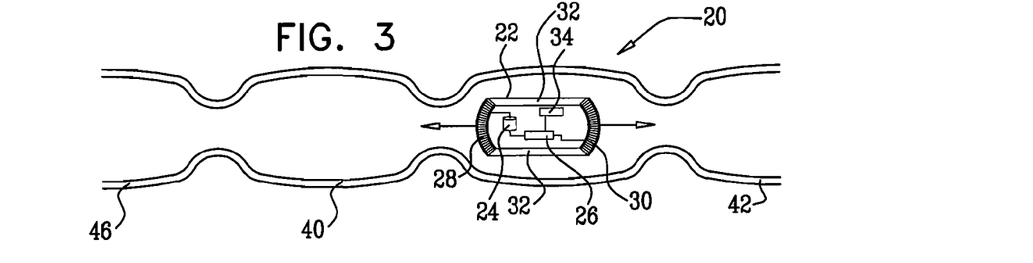
FIG. 3 is a schematic illustration of the capsule within a gastrointestinal tract, in accordance with an embodiment of the present invention.

Reference is now made to FIG. 3, which is a schematic illustration of capsule 22 in motion within intestine 40 of the subject, in accordance with an embodiment of the present invention. Control unit 26 drives a current between electrode 28 and electrode 30 that is configured to induce reverse intestinal peristalsis.

Figure 4:
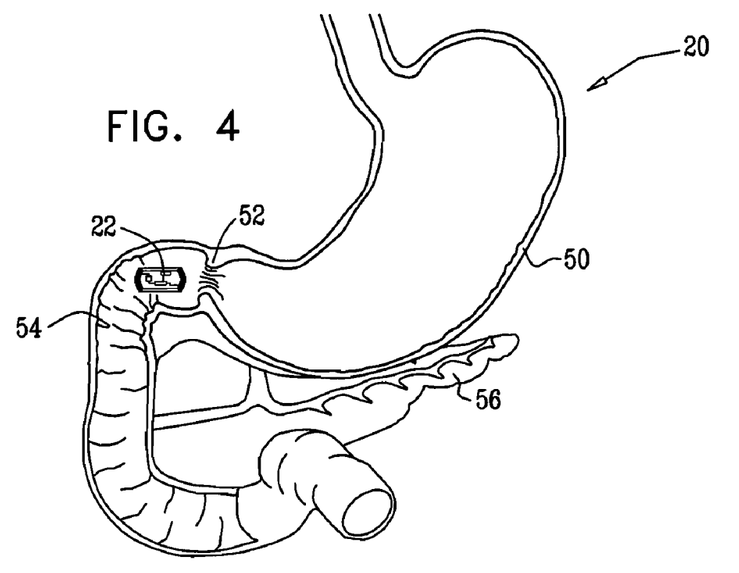
FIGS. 4-6 are schematic illustrations of the capsule within a duodenum, in accordance with respective embodiments of the present invention.

Reference is now made to FIGS. 1A-D and 4, which are schematic illustrations of capsule 22, in accordance with respective embodiments of the present invention. FIG. 4 shows capsule 22 in duodenum 54 in a vicinity of pyloric sphincter 52 of stomach 50. Sensor 34 of capsule 22 is typically configured to identify proximity of capsule 22 to pyloric sphincter 52 by electromyographically sensing contraction of pyloric sphincter 52. Responsively, control unit 26 of capsule 22 drives a current between the electrodes of FIGS. 1A-D to stimulate reverse intestinal peristalsis, maintaining capsule 22 in the vicinity of pyloric sphincter 52 of the subject for a period typically having a duration between about 1 min and about 30 min, or between about 30 min and about 180 min. During this time, a subset of electrodes (described hereinabove with reference to FIGS. 1A-D) drives a current into pyloric sphincter 54 effecting a contraction of pyloric sphincter 52. The rate of gastric emptying by stomach 50 is consequently reduced, and a feeling of satiety is generated within the subject.

In some embodiments, a subset of electrodes (described hereinabove with reference to FIGS. 1A-D) drives a current into the vagus nerve of the subject to induce contraction of pyloric sphincter 52, independently of the proximity of capsule 22 to pyloric sphincter 52.

Figure 5:
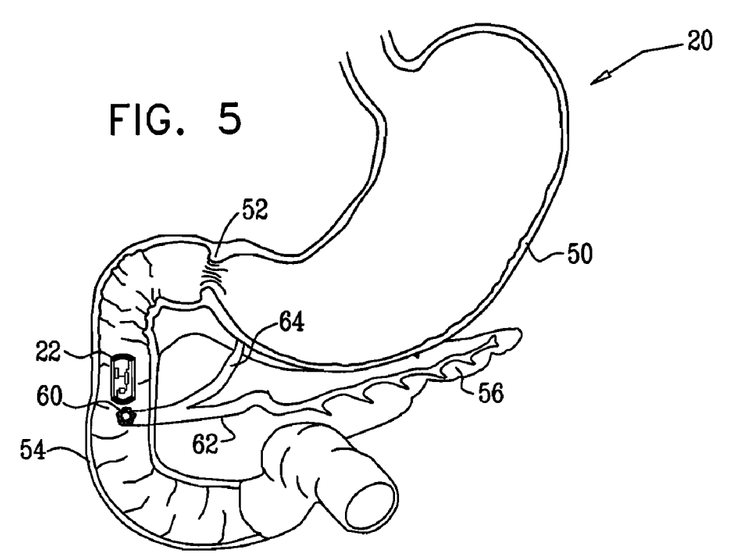

Reference is now made to FIGS. 1A-D and FIG. 5, which are schematic illustrations of capsule 22, in accordance with respective embodiments of the present invention. FIG. 5 shows capsule 22 remaining in duodenum 54 in a vicinity of sphincter of Oddi 60 of the subject. Sensor 34 of capsule 22 identifies proximity of capsule 22 to sphincter of Oddi 60 by electromyographically sensing the presence or absence of contraction of sphincter of Oddi 60. Alternatively or additionally, sensor 34 senses a pH of the external surrounding of capsule 22. A pH of between 4.0 and 7.0 is detected by sensor 34, indicative of capsule 22 being located distal to sphincter of Oddi 60, and sensor 34 generates a sensor signal. In response to the generated signal, control unit 26 of capsule 22 drives a current between the electrodes of FIGS. 1A-D to induce reverse intestinal peristalsis, maintaining capsule 22 in the vicinity of sphincter of Oddi 60 for a period typically having a duration between about 1 min and about 30 min, or between about 30 min and about 180 min.

During the duration of time in which capsule 22 is in the vicinity of sphincter of Oddi 60, a subset of electrodes (described hereinabove with reference to FIGS. 1A-D) drives a current into sphincter of Oddi 60, effecting a contraction of sphincter of Oddi 60. The contraction reduces a rate of digestive fluid emptying from pancreatic duct 62 and bile duct 64, through sphincter of Oddi 60, into duodenum 54. Contraction of sphincter of Oddi 60 and reducing the rate of digestive fluid emptying into duodenum 54, reduces metabolism of fats and carbohydrates.

Figure 6:
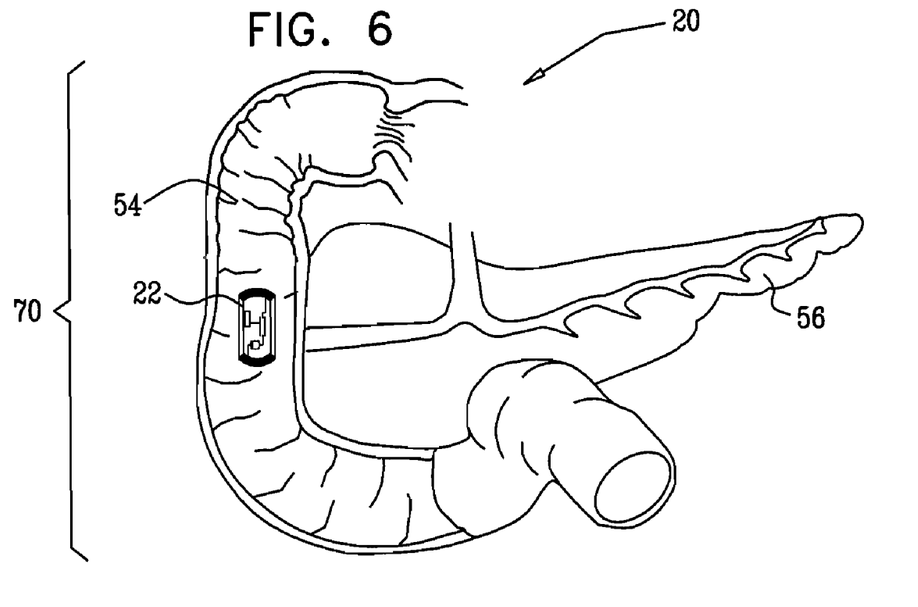

Reference is now made to FIGS. 1A-D and FIG. 6, which are schematic illustrations of capsule 22, in accordance with respective embodiments of the present invention. FIG. 6 shows capsule 22 in duodenum 54 in a segment 70 of duodenum 54, in a position to stimulate pancreas 56. Reverse intestinal peristalsis is actuated by control unit 26 of capsule 22, which drives a current between some of the electrodes of FIGS. 1A-D to stimulate muscles of intestine 40, maintaining capsule 22 in segment 70 of the subject for a period typically having a duration between about 1 min and about 30 min, or between about 30 min and about 180 min.

During the duration of time in which capsule 22 is in segment 70, a subset of electrodes (described hereinabove with reference to FIGS. 1A-D) stimulates pancreas 56 by driving a current into pancreas 56 through the wall of the intestine. For some applications, sensor 34 is configured to detect a state of pancreas 56, or receive a transmission related to a state of pancreas 56, and generate a sensing signal in response thereto. In response to the signal, capsule 22 modulates insulin production by stimulating pancreas 56.

The embodiment in FIGS. 4-6 can be practiced using any configuration of capsule 22 as shown in FIGS. 1A-D.

Figure 7:
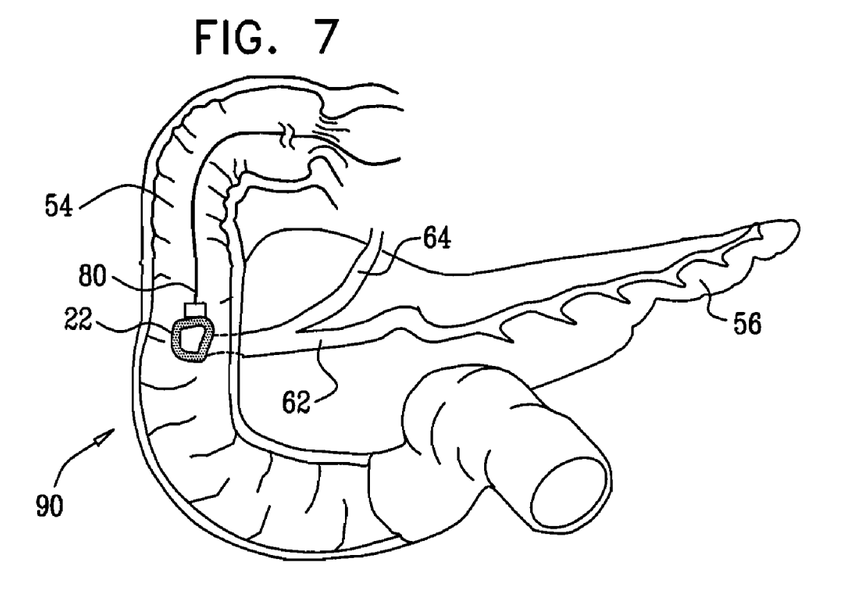
FIG. 7 is a schematic illustration of electrodes within the duodenum, in accordance with an embodiment of the present invention.

Reference is now made to FIG. 7, which is a schematic illustration of apparatus 90 comprising an implantable electrode 80 configured to be implanted on duodenum 56 of the subject, in accordance with an embodiment of the present invention. Electrode 80, shown as an individual electrode by way of example, comprises one or more electrodes which are configured to stimulate and induce contraction of sphincter of Oddi 60 for a period typically having a duration between about 1 min and about 30 min, or between about 30 min and about 180 min. The contraction reduces a rate of digestive fluid emptying from pancreatic duct 62 and bile duct 64, through sphincter of Oddi 60, and into duodenum 54. Contraction of sphincter of Oddi 60 and reducing the rate of digestive fluid emptying into duodenum 54, reduces the metabolism of fats and carbohydrates. For some applications, apparatus 90 stimulates sphincter of Oddi 60 on a regular schedule (e.g., a fixed number of minutes per hour), and/or in accordance with detected eating or digestion (e.g., for the first 15 minutes that food is in the duodenum).

For some applications, embodiments described herein are practiced using techniques described in one or more of the references cited hereinabove, which are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
an ingestible capsule;
one or more electrodes coupled to the capsule; and
a control unit configured to maintain the capsule in a vicinity of a designated site of a subject by driving at least a subset of the electrodes to apply a current that induces reverse intestinal peristalsis in the subject.

2. The apparatus according to claim 1, wherein the one or more electrodes are configured to stimulate reverse peristalsis of intestine of the subject.

3. The apparatus according to claim 1, wherein the one or more electrodes comprise a plurality of electrodes.

4. The apparatus according to claim 1, wherein the control unit is configured to maintain the capsule in a vicinity of a sphincter of Oddi.

5. The apparatus according to claim 4, wherein the control unit is configured to maintain the capsule in a vicinity of the sphincter of Oddi of the subject for a period having a duration between 1 min and 30 min.

6. The apparatus according to claim 4, wherein the control unit is configured to maintain the capsule in a vicinity of the sphincter of Oddi of the subject for a period having a duration between 30 min and 180 min.

7. The apparatus according to claim 4, wherein the control unit is configured to maintain the capsule in the vicinity of the sphincter of Oddi by inducing repeated proximal motions of the capsule within a duodenum of the subject following respective distal motions of the capsule that are due to natural peristalsis.

8. The apparatus according to claim 4, wherein the control unit is configured to drive at least one of the one or more electrodes to apply a current that induces contraction of the sphincter of Oddi.

9. The apparatus according to claim 1, wherein the control unit is configured to maintain the capsule in a vicinity of a pyloric sphincter of the subject.

10. The apparatus according to claim 9, wherein the control unit is configured to maintain the capsule in a vicinity of the pyloric sphincter of the subject for a period having a duration between 1 min and 30 min.

11. The apparatus according to claim 9, wherein the control unit is configured to maintain the capsule in a vicinity of the pyloric sphincter of the subject for a period having a duration between 30 min and 180 min.

12. The apparatus according to claim 9, wherein the control unit is configured to induce a feeling of satiety of the subject by driving at least one of the one or more electrodes to apply a stimulating current that induces contraction of the pyloric sphincter.

13. The apparatus according to claim 12, wherein the control unit is configured to reduce a rate of gastric emptying of the subject by applying the stimulating current to the pyloric sphincter.

14. The apparatus according to claim 1, wherein the control unit is configured to maintain the capsule in a segment of the intestine that surrounds a pancreas of the subject, and wherein the control unit is configured to stimulate the pancreas of the subject by driving at least one of the one or more electrodes to apply a stimulating current to the pancreas.

15. The apparatus according to claim 14, wherein the control unit is configured to maintain the capsule in the segment for a period having a duration between 1 min and 30 min.

16. The apparatus according to claim 14, wherein the control unit is configured to maintain the capsule in the segment for a period having a duration between 30 min and 180 min.

17. The apparatus according to claim 14, wherein the control unit is configured to maintain the capsule within the segment of the intestine by inducing repeated proximal motions of the capsule within a duodenum of the subject following respective distal motions of the capsule that are due to natural peristalsis.

18. The apparatus according to claim 1, comprising a sensor configured to sense a location of the capsule and generate a signal in response thereto.

19. The apparatus according to claim 18, wherein the sensor is configured to detect electrical activity of a duodenum of the subject.

20. The apparatus according to claim 19, wherein the sensor is configured to detect slow waves indicative of the electrical activity.

21. The apparatus according to claim 19, wherein the sensor is configured to detect spikes indicative of the electrical activity.

22. The apparatus according to claim 18, wherein the capsule comprises a pulse generator, and wherein the pulse generator is configured to be activated in response to the signal.

23. The apparatus according to claim 22, wherein the pulse generator is configured to cyclically reverse polarity of a plurality of pulses driven through the one or more electrodes.

24. The apparatus according to claim 22, wherein the pulse generator is configured to generate a waveform having an amplitude of between 1 mA and 20 mA.

25. The apparatus according to claim 22, wherein the pulse generator is configured to generate a waveform having a pulse duration of between 100 us and 1000 us.

26. The apparatus according to claim 22, wherein the pulse generator is configured to generate a waveform having a pulse duration of between 1 ms and 10 ms.

27. The apparatus according to claim 22, wherein the pulse generator is configured to generate a waveform having a pulse frequency of between 1 Hz and 10 Hz.

28. The apparatus according to claim 22, wherein the pulse generator is configured to generate a waveform having a pulse frequency of between 10 Hz and 100 Hz.

29. The apparatus according to claim 22, wherein the pulse generator is configured to generate a waveform having a burst length of between 100 ms and 1 s.

30. The apparatus according to claim 22, wherein the pulse generator is configured to generate a waveform having a duration between bursts thereof of between 1 s and 10 s.

31. The apparatus according to claim 22, wherein the pulse generator is configured to be activated for a stimulation duration of between 1 min and 30 min.

32. The apparatus according to claim 22, wherein the pulse generator is configured to be activated for a stimulation duration of between 30 min and 180 min.

33. The apparatus according to claim 18, wherein the sensor comprises at least one element selected from the group consisting of: a pH sensor, an electromyography sensor, and an accelerometer.

34. The apparatus according to claim 33, wherein the sensor comprises the pH sensor, and wherein the pH sensor comprises at least one of the one or more electrodes.

35. The apparatus according to claim 33, wherein the sensor comprises the electromyography sensor, and wherein the electromyography sensor is configured to detect sphincter contraction.

36. The apparatus according to claim 35, wherein the sensor is configured to detect slow waves indicative of electrical activity of the sphincter.

37. The apparatus according to claim 35, wherein the sensor is configured to detect spikes indicative of electrical activity of the sphincter.

38. The apparatus according to claim 35, wherein the electromyography sensor is configured to detect a contraction of a sphincter of Oddi.

39. The apparatus according to claim 35, wherein the electromyography sensor is configured to detect contraction of a pyloric sphincter of the subject.

40. Apparatus, comprising:
one or more implantable electrodes configured to be implanted at a sphincter of Oddi of a subject; and
a control unit, configured to drive the electrodes to apply a current that induces contraction of the sphincter of Oddi.

41. The apparatus according to claim 40, wherein the control unit is configured to drive the one or more electrodes to apply the current to the sphincter of Oddi for a period having a duration between 1 min and 30 min.

42. The apparatus according to claim 40, wherein the control unit is configured to drive the one or more electrodes to apply the current to the sphincter of Oddi for a period having a duration between 30 min and 180 min.

43. A method, comprising:
inducing reverse intestinal peristalsis in a subject by electrical stimulation; and
configuring the stimulation to maintain an ingestible capsule in a vicinity of a pyloric sphincter of the subject.

44. The method according to claim 43, comprising ingesting the capsule prior to eating by the subject.

45. The method according to claim 43, comprising ingesting the capsule prior to sleeping by the subject.

46. The method according to claim 43, wherein configuring the stimulation to maintain the capsule in the vicinity of the pyloric sphincter comprises identifying proximity of the capsule to the pyloric sphincter by sensing a contraction of the pyloric sphincter.

47. The method according to claim 46, wherein sensing a contraction of the pyloric sphincter comprises electromyographically sensing.

48. The method according to claim 47, wherein electromyographically sensing comprises detecting slow waves indicative of electrical activity of the pyloric sphincter.

49. The method according to claim 47, wherein electromyographically sensing comprises detecting spikes indicative of electrical activity of the pyloric sphincter.

50. The method according to claim 43, comprising driving a current into the pyloric sphincter configured to reduce a rate of gastric emptying of the subject.

51. The method according to claim 50, wherein driving the current comprises inducing a feeling of satiety of the subject.

52. The method according to claim 50, wherein driving the current comprises stimulating a vagus nerve of the subject.

53. The method according to claim 50, wherein driving the current comprises effecting a contraction of the pyloric sphincter.

54. The method according to claim 50, wherein driving the current comprises driving the current for a period having a duration between 1 min and 30 min.

55. The method according to claim 50, wherein driving the current comprises driving the current for a period having a duration between 30 min and 180 min.

56. The method according to claim 50, wherein driving the current comprises generating a waveform having an amplitude of between 1 mA and 20 mA.

57. The method according to claim 50, wherein driving the current comprises generating a waveform having a pulse duration of between 100 us and 1000 us.

58. The method according to claim 50, wherein driving the current comprises generating a waveform having a pulse duration of between 1 ms and 10 ms.

59. The method according to claim 50, wherein driving the current comprises generating a waveform having a pulse frequency of between 1 Hz and 10 Hz.

60. The method according to claim 50, wherein driving the current comprises generating a waveform having a pulse frequency of between 10 Hz and 100 Hz.

61. The method according to claim 50, wherein driving the current comprises generating a waveform having a burst length of between 100 ms and 1000 ms.

62. The method according to claim 50, wherein driving the current comprises generating a waveform having a duration between bursts thereof of between 1 s and 10 s.

63. A method, comprising:
inducing reverse intestinal peristalsis in a subject by electrical stimulation; and
configuring the stimulation to maintain an ingestible capsule in a vicinity of a sphincter of Oddi of the subject.

64. The method according to claim 63, wherein configuring the stimulation comprises maintaining the capsule in the vicinity of the sphincter of Oddi by inducing repeated proximal motions of the capsule within a duodenum of the subject following respective distal motions of the capsule that are due to natural peristalsis.

65. The method according to claim 63, wherein configuring the stimulation to maintain the capsule in the vicinity of the sphincter of Oddi comprises identifying proximity of the capsule to the sphincter of Oddi by sensing a contraction of the sphincter of Oddi.

66. The method according to claim 65, wherein sensing the contraction of the sphincter of Oddi comprises electromyographically sensing.

67. The method according to claim 65, wherein electromyographically sensing comprises detecting slow waves indicative of electrical activity of the pyloric sphincter.

68. The method according to claim 65, wherein electromyographically sensing comprises detecting spikes indicative of electrical activity of the pyloric sphincter.

69. The method according to claim 63, comprising driving a current into the sphincter of Oddi configured to reduce emptying of a digestive liquid into a duodenum of the subject.

70. The method according to claim 69, wherein driving the current comprises effecting a contraction of the sphincter of Oddi.

71. The method according to claim 69, wherein driving the current comprises driving the current for a period having a duration between 1 min and 30 min.

72. The method according to claim 69, wherein driving the current comprises driving the current for a period having a duration between 30 min and 180 min.

73. The method according to claim 63, wherein maintaining the capsule comprises sensing a parameter of external surroundings of the capsule, and generating a signal in response thereto.

74. The method according to claim 73, wherein sensing the parameter of the external surroundings comprises pH sensing.

75. The method according to claim 74, wherein pH sensing comprises:
detecting a pH of between 4.0 and 7.0 distal to the capsule; and
identifying that the capsule is at a location within a duodenum of the subject distal to the sphincter of Oddi in response to the detecting.

76. The method according to claim 75, comprising inducing a reverse peristaltic wave by stimulating muscle of the intestine in response to the identifying.

77. A method, comprising:
inducing reverse intestinal peristalsis in a subject by electrical stimulation; and
configuring the stimulation to maintain an ingestible capsule in a segment of the small intestine surrounding a pancreas of the subject.

78. The method according to claim 77, wherein maintaining the capsule in the segment comprises inducing repeated proximal motions of the capsule within a duodenum of the subject following respective distal motions of the capsule.

79. The method according to claim 77, wherein maintaining the capsule in the segment comprises maintaining the capsule in the segment for a period having a duration between 1 min and 180 min.

80. The method according to claim 77, comprising stimulating the pancreas by the capsule, when the capsule is in the segment.

81. The method according to claim 80, wherein stimulating the pancreas comprises modulating insulin production of the pancreas.

82. The method according to claim 80, comprising detecting a state of the pancreas, and wherein stimulating the pancreas comprises stimulating the pancreas in response to the detecting.

* * * * *